| (12) | United States Patent | (10) Patent No.: | US 10,177,639 B2 |
|---|---|---|---|
| | Takahashi et al. | (45) Date of Patent: | *Jan. 8, 2019 |

(54) ACTUATOR AND ELECTRIC BEAUTY APPLIANCE

(71) Applicants: Yuki Takahashi, Tokyo (JP); Shigenori Inamoto, Tokyo (JP)

(72) Inventors: Yuki Takahashi, Tokyo (JP); Shigenori Inamoto, Tokyo (JP)

(73) Assignee: MITSUMI ELECTRIC CO., LTD., Tokyo (JP)

( * ) Notice: Subject to any disclaimer, the term of this patent is extended or adjusted under 35 U.S.C. 154(b) by 183 days.

This patent is subject to a terminal disclaimer.

(21) Appl. No.: 15/207,560

(22) Filed: Jul. 12, 2016

(65) Prior Publication Data

US 2016/0322889 A1 Nov. 3, 2016

Related U.S. Application Data

(63) Continuation of application No. 14/069,552, filed on Nov. 1, 2013, now Pat. No. 9,419,507.

(30) Foreign Application Priority Data

Nov. 1, 2012 (JP) .................................. 2012-242180

(51) Int. Cl.
*H02K 33/02* (2006.01)
*H02K 33/16* (2006.01)
(Continued)

(52) U.S. Cl.
CPC ............. *H02K 33/02* (2013.01); *A61C 17/34* (2013.01); *A61C 17/3481* (2013.01);
(Continued)

(58) Field of Classification Search
CPC ...... H02K 21/145; H02K 21/22; H02K 33/02; H02K 33/16
(Continued)

(56) References Cited

U.S. PATENT DOCUMENTS

| 4,227,164 A | * | 10/1980 | Kitahara | ................. H01F 7/145 |
|---|---|---|---|---|
| | | | | 310/36 |
| 4,319,823 A | * | 3/1982 | Hashimoto | ............... G03B 9/08 |
| | | | | 310/37 |

(Continued)

FOREIGN PATENT DOCUMENTS

| JP | 3243529 B2 | 1/2002 |
|---|---|---|
| JP | 2002-078310 A | 3/2002 |

(Continued)

OTHER PUBLICATIONS

Extended European Search Report dated Feb. 25, 2014 for the corresponding European Patent Application No. 13191039.0.

(Continued)

*Primary Examiner* — John K Kim

(74) *Attorney, Agent, or Firm* — Brundidge & Stanger, P.C.

(57) ABSTRACT

An actuator includes a movable body including a cylindrical magnet portion, an immovable body including pole tooth faces and a coil, and a torsion coil spring supporting a movable body to the immovable body. The coil receives an alternating current of a frequency substantially equal to a resonance frequency of the movable body and excites the pole tooth faces to have alternately different polarities in the circumferential direction. One end of the torsion coil spring is fixed to one end of a rotary shaft of the movable body and other end is fixed to the immovable body. The torsion direction of the torsion coil spring is arranged to be coaxial with the rotary shaft. The torsion coil spring supports the (Continued)

movable body to enable the movable body to vibrate at the resonance frequency of the movable body.

4 Claims, 14 Drawing Sheets

(51) Int. Cl.
    *A61C 17/34*     (2006.01)
    *B26B 19/38*     (2006.01)
    *H02K 21/14*     (2006.01)
    *H02K 21/22*     (2006.01)

(52) U.S. Cl.
    CPC ......... *B26B 19/3873* (2013.01); *H02K 33/16* (2013.01); *H02K 21/145* (2013.01); *H02K 21/22* (2013.01)

(58) Field of Classification Search
    USPC .......................................................... 310/38
    See application file for complete search history.

(56) References Cited

U.S. PATENT DOCUMENTS

| | | | |
|---|---|---|---|
| 5,189,751 A | 3/1993 | Giuliani et al. | |
| 5,561,486 A * | 10/1996 | SanGregory | G03B 9/08 335/125 |
| 6,833,639 B2 * | 12/2004 | Lau | A61C 17/3418 310/17 |
| 6,960,848 B2 * | 11/2005 | Naganuma | G03B 7/10 310/37 |
| 7,218,018 B2 | 5/2007 | Hasegawa et al. | |
| 7,443,058 B2 | 10/2008 | Shimizu et al. | |
| 7,474,018 B2 | 1/2009 | Shimizu et al. | |
| 7,544,003 B2 * | 6/2009 | Huang | G03B 9/08 310/103 |
| 7,732,952 B1 * | 6/2010 | Taylor | A61C 17/20 15/22.1 |
| 7,960,877 B2 * | 6/2011 | Luo | A61C 17/3418 15/22.1 |
| 8,970,072 B2 | 3/2015 | Headstrom | |
| 9,419,507 B2 * | 8/2016 | Takahashi | H02K 33/16 |
| 2005/0200207 A1 | 9/2005 | Hasegawa et al. | |
| 2007/0040457 A1 | 2/2007 | Shimizu et al. | |
| 2007/0145832 A1 | 6/2007 | Shimizu et al. | |
| 2007/0170877 A1 | 7/2007 | Hasegawa et al. | |
| 2010/0306934 A1 | 12/2010 | Headstrom | |
| 2014/0117788 A1 | 5/2014 | Takahashi et al. | |
| 2015/0200582 A1 | 7/2015 | Headstrom | |
| 2016/0322889 A1 * | 11/2016 | Takahashi | H02K 33/16 |

FOREIGN PATENT DOCUMENTS

| | | |
|---|---|---|
| JP | 2004-194499 A | 7/2004 |
| JP | 2004-343930 A | 12/2004 |
| JP | 2004-343933 A | 12/2004 |
| JP | 2011-508579 A | 3/2011 |

OTHER PUBLICATIONS

Foreign Office Action dated Feb. 10, 2015.
Japanese Office Action dated Jul. 7, 2015.

* cited by examiner

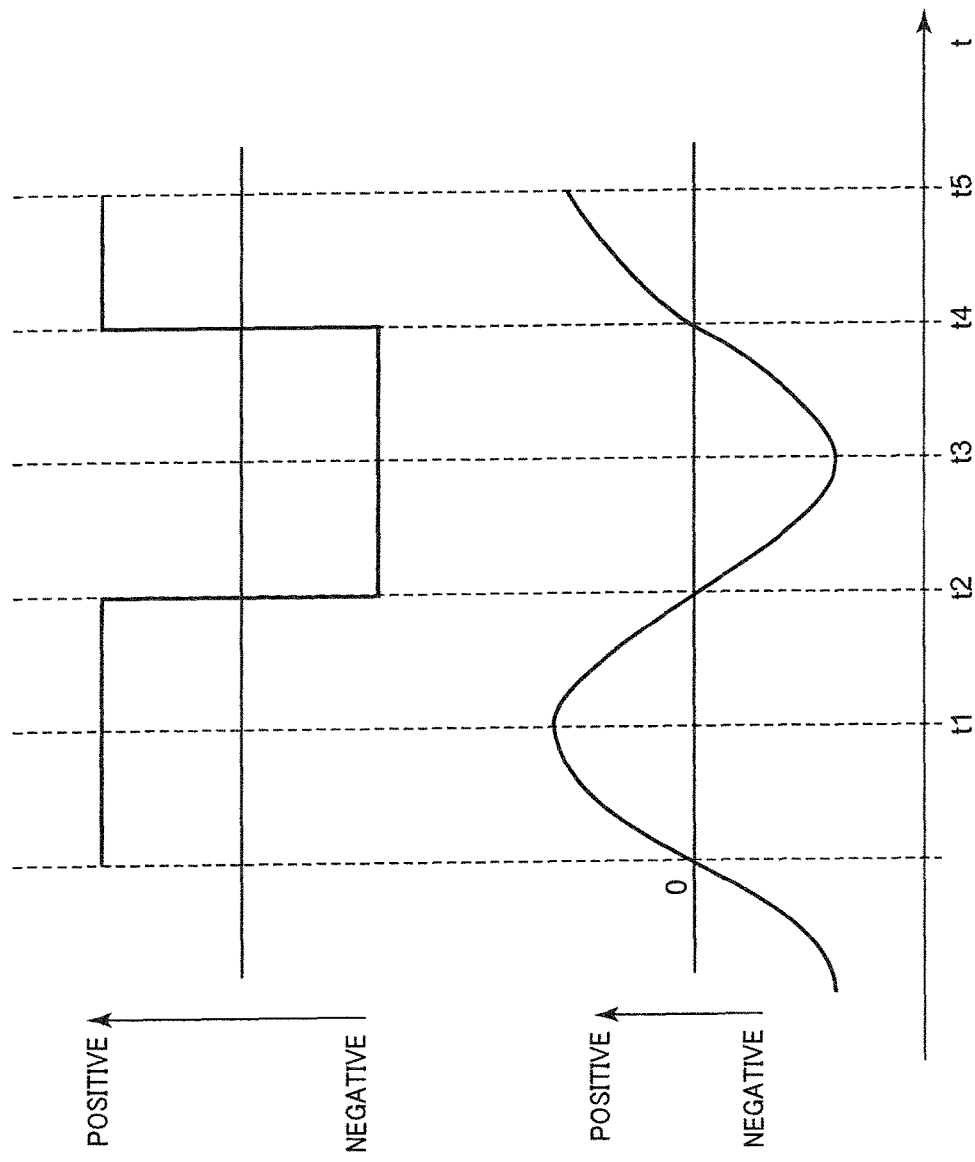

ACTUATOR AND ELECTRIC BEAUTY APPLIANCE

CROSS REFERENCE TO RELATED APPLICATIONS

The present application is a Continuation of application Ser. No. 14/069,552, filed Nov. 1, 2013; which claims the benefit of Japanese Patent Application No. 2012-242180 filed on Nov. 1, 2012, the disclosure of which including the specification, drawings and abstract is incorporated herein by reference in its entirety.

BACKGROUND OF THE INVENTION

1. Field of the Invention

The present invention relates to an actuator of a rotary resonance type and an electric beauty appliance.

2. Description of Related Art

Electric toothbrushes as electric beauty appliances known in the art include a bass brushing toothbrush that is contacted obliquely with a boundary between teeth and gums (at an angle of approximately 45 degrees) and vibrated laterally by reciprocal linear motion; and a rolling brushing toothbrush that rotates reciprocally (in forward and reverse directions) about a shaft within a predetermined angular range in such a manner that the toothbrush moves from gums to teeth and vice versa in a rotational manner.

For driving these toothbrushes, many structures have been used for converting the typical rotary motion of a rotary DC motor into a reciprocal linear or rotary motion, via a motion direction converting mechanism. Furthermore, besides these structures, structures are known wherein the toothbrush is moved reciprocally linearly by means of a linear drive actuator, or the toothbrush is rotated reciprocally by making a resonance vibrating mechanism, which is separated from a drive source including an actuator, resonate by the vibration of the actuator.

In a structure wherein a toothbrush is moved reciprocally linearly by means of a linear drive actuator, as shown in Japanese Patent Application Laid-Open No. 2002-078310, the linear drive actuator directly produces reciprocal vibration in the axial direction of an output shaft that is directly connected to a brush part so as to realize bass brushing. This configuration generates no power loss due to a motion converting mechanism thus enabling fast vibration.

Furthermore, a structure having an actuator and a resonance vibrating mechanism separated from a drive source including the actuator is disclosed in a vibration toothbrush disclosed in Japanese Patent No. 3243529. Japanese Patent No. 3243529 realizes rolling brushing by vibrating the resonance vibrating mechanism having a lever arm by a drive section with an electro magnet and a permanent magnet and moving the lever arm that is coaxially connected to a toothbrush part in swinging motion.

Thus, as an actuator to be used for an electric toothbrush and produce reciprocal rotary motion, there remains in the art a need for a high-power actuator with a simpler structure.

SUMMARY OF THE INVENTION

An object of the present invention is to provide an actuator and an electric beauty appliance that can realize high power with a simple structure.

To achieve at least one of the above mentioned objects, an actuator according to one aspect of the present invention comprises:

a movable body including a cylindrical magnet portion having on a circumferential surface thereof alternating N pole faces and S pole faces along a circumferential direction thereof; and an immovable body including pole tooth faces arranged along the circumferential direction so as to face the circumferential surface of the magnet portion, the number of the pole tooth faces being equal to the number of the N pole faces and the S pole faces, and a coil that receives an alternating current of a frequency substantially equal to a resonance frequency of the movable body to excite the pole tooth faces to have alternately different polarities in the circumferential direction, wherein the movable body is held by the immovable body in a rotatable manner, and a neutral position for rotation of the movable body is a position at which center positions of the pole tooth faces in the circumferential direction and boundary positions between the pole faces of the magnet portion face each other.

BRIEF DESCRIPTION OF DRAWINGS

The present invention will become more fully understood from the detailed description given hereinbelow and the appended drawings which are given by way of illustration only, and thus are not intended as a definition of the limits of the present invention, and wherein:

FIG. 7A illustrates a period of an alternating current of pulse waves supplied from an alternating current supplier to a coil in the actuator;

FIG. 7B illustrates a period of an alternating current of sine waves supplied from an alternating current supplier to a coil in the actuator;

DESCRIPTION OF THE PREFERRED EMBODIMENTS

In the following, embodiments of the present invention are described in detail with reference to the accompanying drawings.

Embodiment 1

Figure 1:
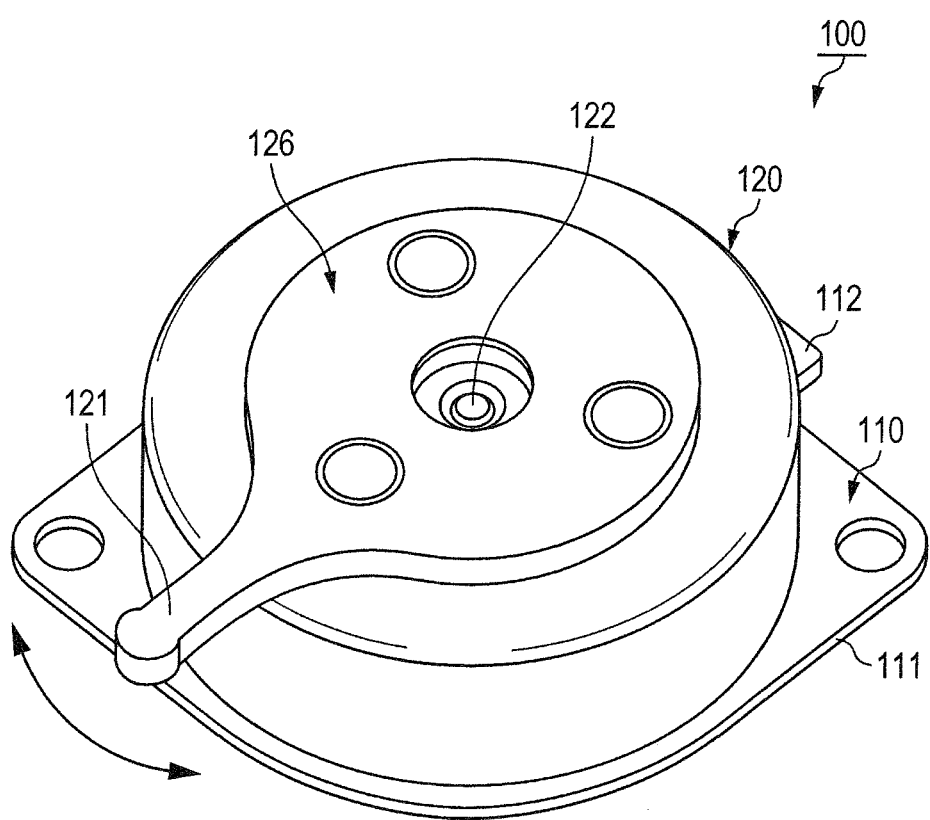
FIG. 1 is a perspective view illustrating an actuator according to Embodiment 1 of the present invention.
Figure 2:
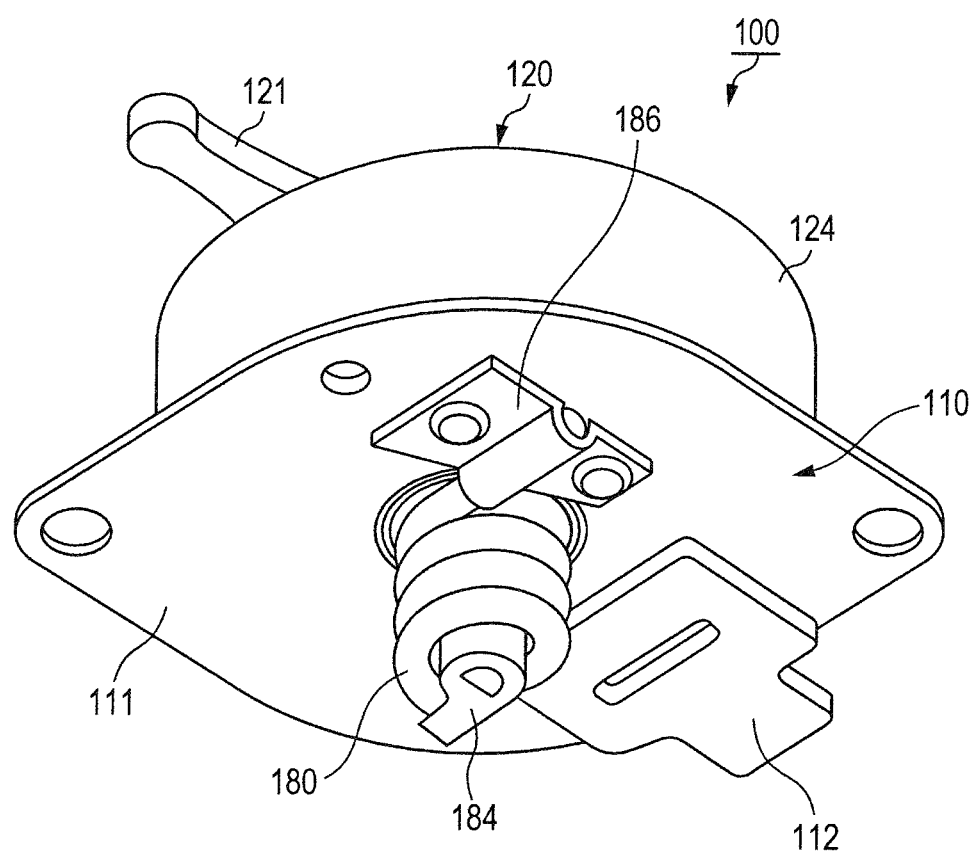
FIG. 2 is a perspective view illustrating a lower surface of the actuator.
Figure 3:
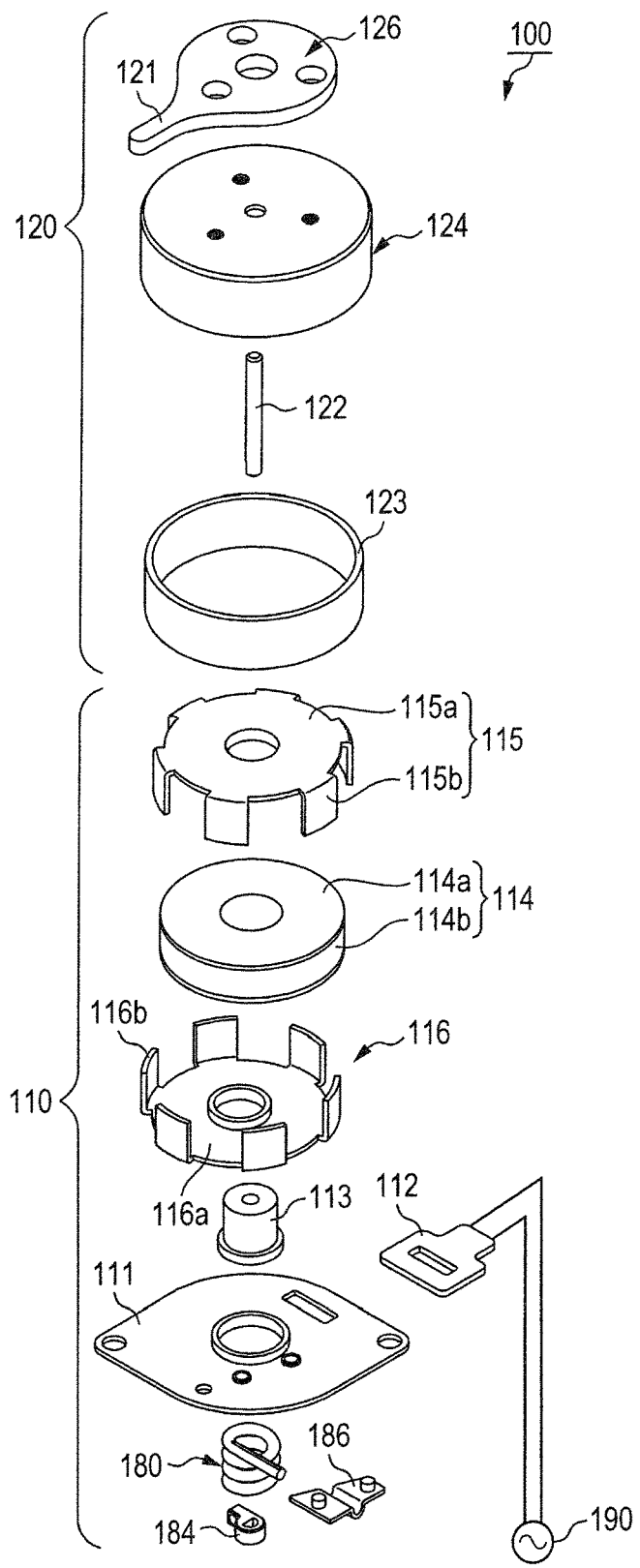
FIG. 3 is an exploded perspective view of main part of the actuator.
Figure 4:
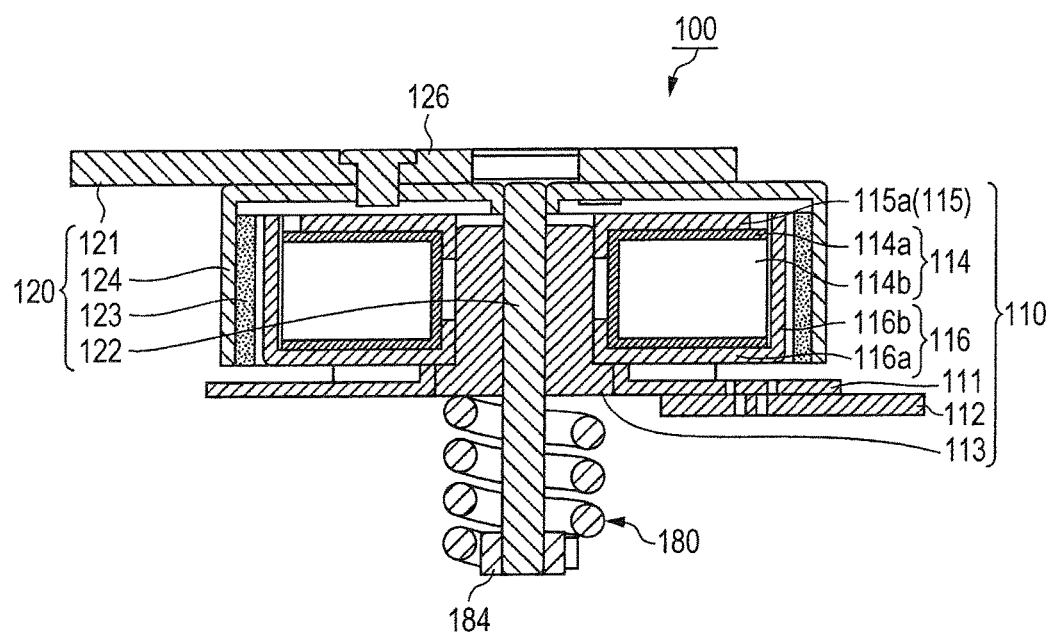
FIG. 4 is a schematic cross-sectional view illustrating a main part configuration in the actuator.

FIG. 1 is a perspective view illustrating an actuator according to Embodiment 1 of the present invention, FIG. 2 is a perspective view illustrating a lower surface of the actuator, and FIG. 3 is an exploded perspective view of main part of the actuator. FIG. 4 is a schematic cross-sectional view illustrating a main component configuration in the actuator.

Actuator 100 illustrated in FIGS. 1 and 2 has immovable body 110, movable body 120, elastic member (elastic support) 180 that supports movable body 120 to immovable body 110 in a movable manner (see FIG. 2) and alternating current supplier 190 (see FIG. 3).

In actuator 100 illustrated in FIGS. 1 and 2, movable body 120 (see FIG. 2) moves with respect to immovable body 110 by power supplied from alternating current supplier 190, output arm (hereinafter "arm") 121 of movable body 120 rotates in forward and reverse directions (directions of arrow in FIG. 1) within a predetermined angular range, which results in a reciprocal rotary vibration output to the outside.

As illustrated in FIGS. 3 and 4, immovable body 110 has base plate 111, substrate 112, bearing 113, annular coil portion 114 and comb-toothed upper and lower yokes 115 and 116 having pole teeth (pole tooth faces) 115b and 116b arranged along the outer circumferential surface of coil portion 114.

In immovable body 110, substrate 112 is attached to base plate 111. A base end portion of bearing 113 is inserted in an opening provided in the center of base plate 111, and bearing 113 is fixed in an upright state with respect to base plate 111.

Rotary shaft 122 of movable body 120 is inserted in bearing 113, and bearing 113 supports rotary shaft 122 in a rotatable manner.

Coil portion 114 enclosed by upper and lower yokes 115 and 116 is arranged in the outer circumferential surface of bearing 113.

Coil portion 114 is formed by winding coil 114b in the circumferential direction of bobbin 114a. Bobbin 114a and coil 114b are used together to create a drive source of actuator 100. Bobbin 114a is coaxial with rotary shaft 122 and coil 114b. The winding wire of coil 114b is connected to substrate 112 and connected to an external terminal through substrate 112. An alternating current (alternating current voltage) is supplied from alternating current supplier 190 to coil 114b through the external terminal.

Upper and lower yokes 115 and 116 are made of a magnetic material and respectively have comb-toothed pole teeth 115b and 116b which extend vertically from the outer edge of annular body plate portions 115a and 116a. Upper and lower yokes 115 and 116 are arranged in a mutually non-contact manner so as to sandwich coil portion 114 in the axial direction of rotary shaft 122. Respective body plate portions 115a and 116a of upper and lower yokes 115 and 116 are arranged facing upper and lower surfaces of coil portion 114 which are spaced apart in the axial direction of rotary shaft 122, and respective pole teeth 115b and 116b of upper and lower yokes 115 and 116 are alternately located so as to enclose the outer circumferential surface of coil portion 114. To be more specific, upper yoke 115 is fitted from the upper side of coil portion 114, its body plate portion 115a faces the upper surface of coil portion 114, and pole teeth 115b are located in a comb tooth manner (spaced at a predetermined interval) along the outer circumferential surface of coil portion 114 from the outer circumferential surface of coil portion 114. Lower yoke 116 is fitted from the lower side of coil portion 114, its body plate portion 116a faces the lower surface of coil portion 114, and pole teeth 116b are uniformly arranged between pole teeth 115b located along the outer circumferential surface of coil portion 114.

The number of poles of pole teeth 115b and 116b of upper and lower yokes 115 and 116 are equal to the number of magnetic poles of magnets 123 (described later) of movable body 120.

With this configuration, when an alternating current is supplied to coil 114b, upper yoke 115 and lower yoke 116 are excited respectively to have mutually different polarities, and respective pole teeth 115b and 116b of upper and lower yokes 115 and 116 are also excited by different polarities. When an alternating current of a frequency substantially equal to an resonance frequency of movable body 120 is supplied from alternating current supplier 190 to coil 114b, pole teeth 115b and 116b are alternately excited to have different polarities. That is, in the outer circumferential surface of coil portion 114, different magnetic pole faces are alternately arranged along the outer circumferential surface.

The polarities of these pole teeth 115b and 116b alternately change by a forward-direction current and a reverse-direction current supplied to coil portion 114.

Magnet 123 of movable body 120 is arranged so as to face pole teeth 115b and 116b arranged along the outer circumferential surface of coil portion 114, at a predetermined distance from the pole teeth 115b and 116b.

Although pole teeth 115b and 116b are configured to have 12 poles, which are the same as a corresponding magnet (described later), the number of poles is not limited to 12 and may be two or more in a variation of the present embodiment. Pole teeth 115b and 116b face the circumferential surface of magnet 123, are arranged over the circumferential direction and have the same number of poles as N poles (N pole faces) and S poles (S pole faces) in magnet 123.

Movable body 120 has rotary shaft 122, magnet 123 and magnet fixing portion 124 that fixes rotary shaft 122 and magnet 123.

Figure 5:
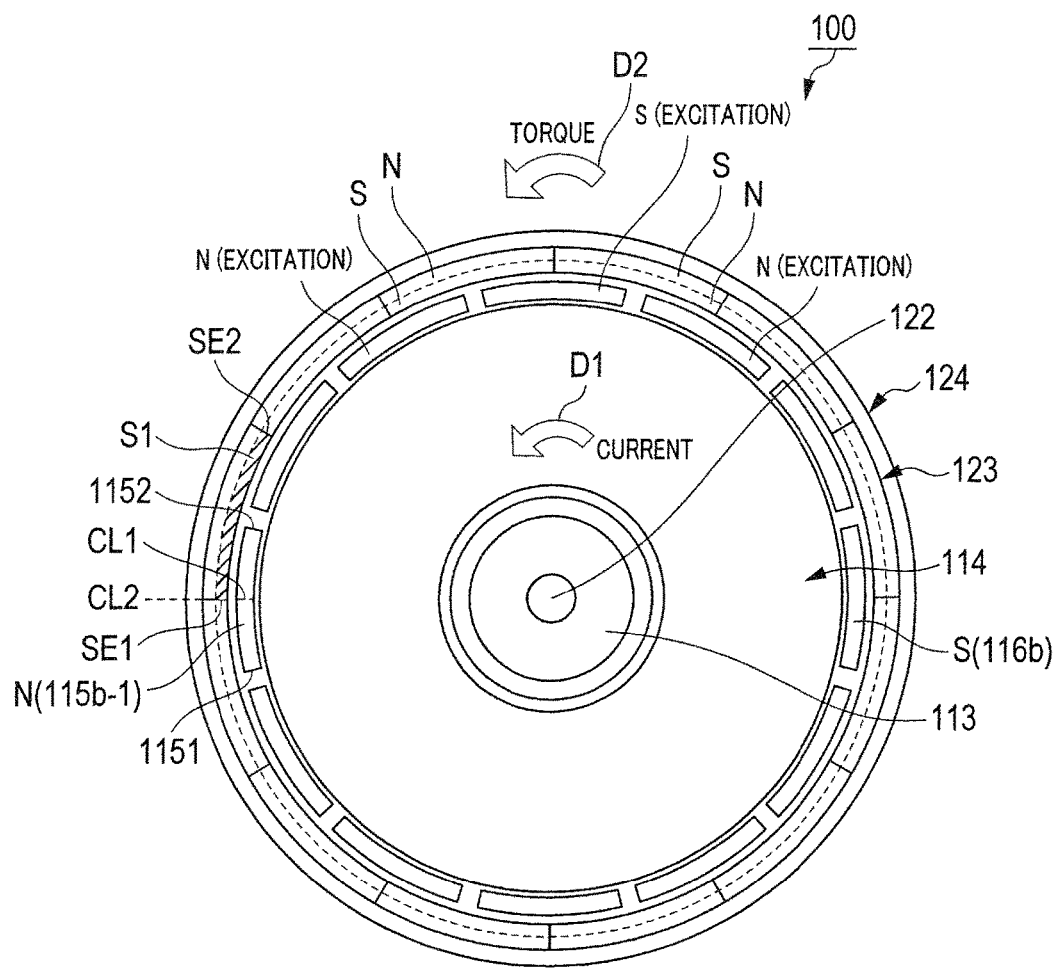
FIG. 5 is a plan cross-sectional view illustrating a magnetic circuit of the actuator.

As illustrated in FIG. 5, magnet 123 is cylindrical and magnetized with multiple (12 in this case) poles, and, for example, a neodymium bond magnet is employed.

To be more specific, magnet 123 is magnetized so as to have magnetic pole faces of alternately-different polarities, like N pole, S pole, N pole, S pole, N pole, . . . , along the circumferential direction in a circumferential surface (an inner circumferential surface in this case) facing pole teeth 115b and 116. The length of each of the magnetized faces of N pole, S pole, . . . in the circumferential direction (here, the direction perpendicular to the rotary shaft in the circumferential direction) is longer than the length of pole teeth 115b and 116b in the circumferential direction. Note that although magnet 123 is configured as a single piece in a cylindrical shape, positions between adjacent magnetized faces at which the polarity is reversed (positions such as edges SE1 and SE2) are expediently shown by partition lines in FIG. 5.

Magnet 123 is fixed to rotary shaft 122 by magnet fixing portion 124 made of a magnetic material.

In the magnetized faces of magnet 123, pole teeth 115b and 116b are located with respect to the magnetized faces of magnet 123 in such a manner that respective center positions CL1 in the circumferential direction coincide positions CL2 (positions at which the magnetized faces S and N are partitioned) between the N magnetized face and the S magnetized face (the N pole face and the S pole face) of magnet 123 in a radial direction with respect to a rotational center. A position at which center position CL1 and position CL2 overlap on the same straight line in the radial direction with respect to rotary shaft 122 (that is, in a radial fashion) is a neutral position for rotation operation (rotation neutral position) of movable body 120. That is, movable body 120 is held by immovable body 110 in a rotatable manner with respect to a position as a rotation neutral position at which center position CL1 in the circumferential direction of respective pole teeth 115b and 116b faces boundary position (partition line) CL2 between the magnetic pole faces of magnet 123. Because actuator 100 includes 12 poles, the rotatable range of movable body 120 with respect to immovable body 110 is a range where the movable body 120 rotates in the forward or reverse direction by an angle of 15 degree from the rotation neutral position.

Magnet fixing portion 124 has a cup shape, formed by e.g. spinning, where a tubular portion extending downwards from the outer edge of a disc-shaped fixing portion body. Magnet 123 is fixed to the inner circumferential surface of this tubular portion.

Output connection portion 126 having arm 121 extending perpendicularly to the rotary shaft is attached to the fixing portion body of magnet fixing portion 124. This output connection portion 126 transmits a drive force to the outside through arm 121.

Moreover, one end of rotary shaft 122 inserted into bearing 113 in a rotatable manner is fixed to the center of the fixing portion body by press fit.

Rotary shaft 122 is fixed to the fixing portion body so as to be coaxial with magnet fixing portion 124.

The other end of rotary shaft 122 is passed through a shaft hole formed in immovable body 110 (base plate 111). This other end is fixed to base plate 111 through elastic member 180 on the back side of base plate 111.

Elastic member 180 elastically supports movable body 120 with respect to immovable body 110. A torsion coil spring is employed as elastic member 180. Rotary shaft 122 is inserted through the center of the torsion coil spring in a rotatable manner. Rotary shaft 122 is coaxial with the torsion coil spring, and it is preferable that rotary shaft 122 is coaxial with the torsion direction.

One end of the torsion coil spring that is elastic member 180 is fixed to rotary shaft 122 by shaft fixing part 184 and the other end is fixed to base plate 111 by base fixing part 186.

Elastic member (torsion coil spring) 180 is positioned in such a manner that on the inner circumferential surface of magnet 123 of movable body 120 the boundary positions between adjacent magnetized faces of different magnetic properties are located at the center in the circumferential direction of respective pole teeth 115b and 116b of immovable body 110.

Moreover, elastic member (torsion coil spring) 180 can acquire a given spring constant with respect to the rotation direction of magnet 123 and movable body 120 is movable in the circumferential direction. It is possible to adjust the resonance frequency in actuator 100 by this elastic member 180.

In actuator 100 of the above configuration, upper and lower yokes 115 and 116, i.e. pole teeth 115b and 116b, are magnetized by the alternating current wave input to coil 114b, and the magnetic attractive force and the magnetic repulsive force are efficiently generated for magnet 123 of movable body 120. In this way, magnet 123 of movable body 120 moves in both directions of the circumferential direction with respect to the center of pole teeth 115b and 116b as the neutral position, and, as a result of this, magnet 123 itself performs reciprocal rotation with respect to rotary shaft 122.

In actuator 100 of the present embodiment, when the inertia of movable body 120 is assumed to J and the spring constant in the torsion direction is assumed to $K_{sp}$, movable body 120 vibrates with respect to immovable body 110 at resonance frequency $f_r$ [Hz] calculated by the following Equation 1.

$$f_r = \frac{1}{2\pi}\sqrt{\frac{K_{sp}}{J}} \qquad \text{(Equation 1)}$$

$f_r$: Resonance frequency [Hz]

In actuator 100 of the present embodiment, an alternating current of a frequency substantially equal to resonance frequency $f_r$ of movable body 120 is supplied to coil 114b by alternating current supplier 190. In this way, it is possible to efficiently drive movable body 120.

Movable body 120 in this actuator 100 is supported by a spring mass system structure supported by immovable body 110 through elastic member 180. Therefore, when the alternating current of the frequency equal to resonance frequency $f_r$ of movable body 120 is supplied to coil 114b, movable body 120 is driven in a resonant condition. The reciprocal rotary vibration generated at this time is transmitted to arm 121 of movable body 120.

Actuator 100 is driven on the basis of the motion equation given by the following Equation 2 and the circuit equation given by the following Equation 3.

$$J\frac{d^2\theta(t)}{dt^2} = K_t i(t) - K_{sp}\theta(t) - D\frac{d\theta(t)}{dt} - T_{Load} \qquad \text{(Equation 2)}$$

$J$: Inertia moment [Kgm²]
$\theta(t)$: Angle [rad]
$K_t$: Torque constant [Nm/A]
$i(t)$: Current [A]
$K_{sp}$: Spring constant [Nm/rad]
$D$: Attenuation coefficient [Nm/(rad/s)]
$T_{Load}$: Load torque [Nm]

$$e(t) = Ri(t) + L\frac{di(t)}{dt} + K_e\frac{d\theta(t)}{dt} \qquad \text{(Equation 3)}$$

$e(t)$: Voltage [V]
$R$: Resistance [Ω]
$L$: Inductance [H]
$K_e$: Counter-electromotive force multiplier [V/(rad/s)]

That is, inertia moment J [Kgm²], rotation angle θ(t) [rad], torque constant $K_t$ [Nm/A], current i(t) [A], spring constant $K_{sp}$ [Nm/rad], attenuation coefficient D [Nm/(rad/s)] and load torque $T_{Load}$ [Nm], and so on, in actuator 100 can be adequately changed as long as Equation 2 is satisfied. Moreover, voltage e(t) [V], resistance R [Ω], inductance L [H] and counter-electromotive force multiplier $K_e$ [V/(rad/s)] can be adequately changed as long as Equation (3) is satisfied.

Figure 6A:
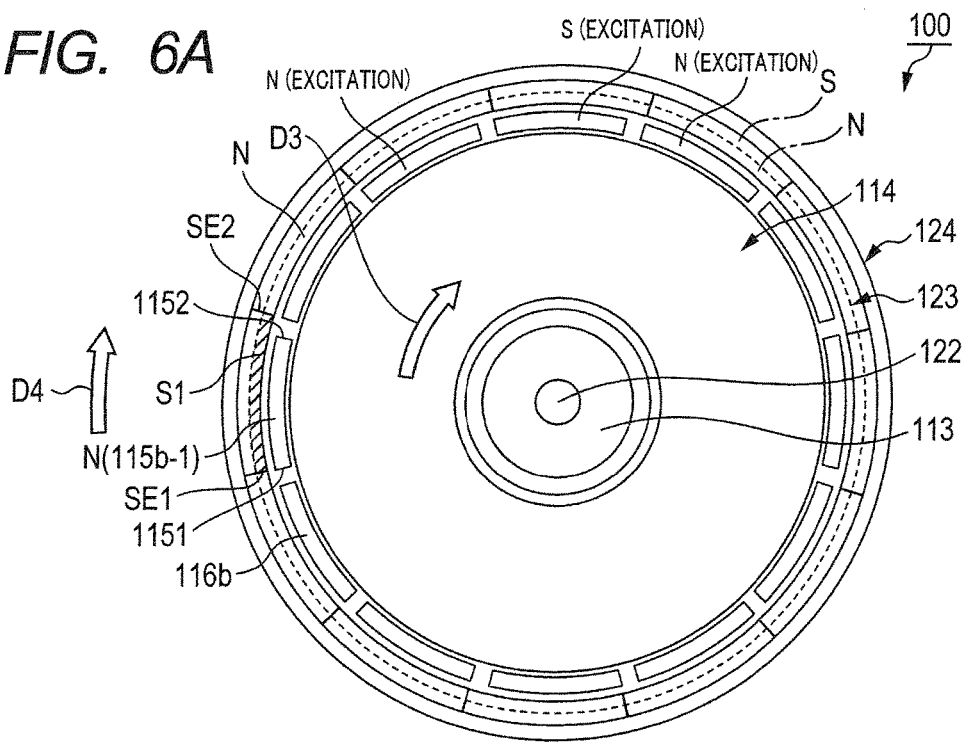
FIG. 6A is a plan cross-sectional view serving to describe an operation of the actuator and illustrating a state where a magnetic surface of a magnet is at a first position.
Figure 6B:
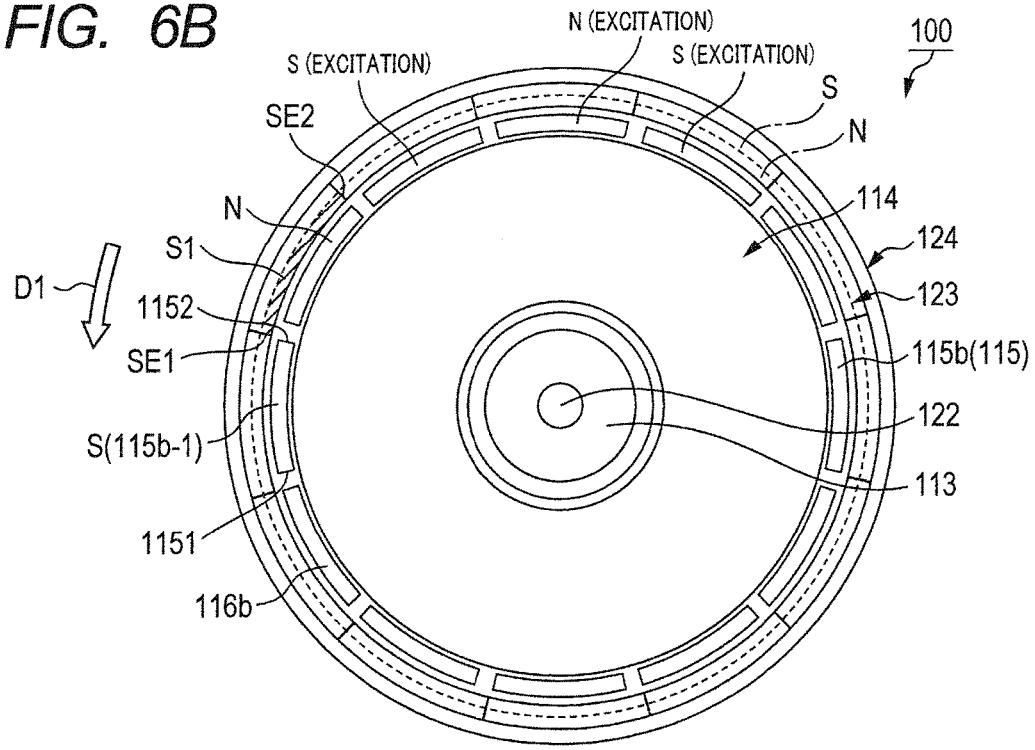
FIG. 6B is a plan cross-sectional view serving to describe an operation of the actuator and illustrating a state where a magnetic surface of a magnet is at a second position.

Next, specific operation of actuator 100 is described. FIGS. 6A and 6B are plan cross-sectional views serving to describe the operation of actuator 100.

A current flows to coil 114b of coil portion 114 in direction D1 indicated by the arrow in FIG. 5 (this direction is referred to as "forward current"). Then, pole teeth 115b of upper yoke 115 are excited and have a polarity (N pole in this case), and pole teeth 116b of lower yoke 116 are excited and have a different polarity (the S pole in this case) from pole teeth 115b. A partition line of magnetic pole faces (S and N) in magnet 123 of movable body 120 is arranged in the center position of the circumferential direction (rotation direction) of each of pole teeth 115b and 116b, that is, at the neutral position, so as to face these pole teeth 115b and 116b. Therefore, the N pole faces are attracted to pole teeth 115b that are the S pole faces over the entire inner circumferential surface of magnet 123, the S pole faces of magnet 123 are attracted to pole teeth 116b that are N pole faces, and the identical poles are repulsed. In this way, the largest torque (arrow D2) is generated over the entire inner circumferential surface of magnet 123 and magnet 123 rotates in the direction of arrow D2 (counterclockwise rotation in this case).

Then, as illustrated in FIG. 6A, each pole face in magnet 123 is about to stop at a facing position with pole teeth 115b and 116b excited by opposing magnetic poles. For example, magnetic pole face S1 is about to stop at a position completely facing the N pole face (pole tooth 115b-1) that is a different pole face on the side of immovable body 110. Moreover, an edge (for example, edge SE1) of a pole face (for example, S1) of magnet 123 is located at this position so as to face an edge side (for example, edge side 1151) located on the rotation direction side of magnet 123 among edge sides spaced apart in the circumferential direction in pole teeth 115b. When magnet 123 is about to reach this position, a torque is also exerted on magnet 123 in the direction (direction of arrow D4) opposite to the direction of arrow D1 by repulsion to a pole tooth of the same magnetic pole close to magnet 123. Moreover, magnet 123 (movable body 120) is in a state where it is biased to the neutral position side by the restoring force of elastic member 180.

In the state illustrated in this FIG. 6A, current (reverse current) in the direction (arrow D3) opposite to the forward current flows in coil portion 114. Then, the polarities of pole teeth 115b and 116b change, that is, pole teeth 115b which have been N poles until then are excited to be S poles and pole teeth 116b which have been S poles until then are excited to be N poles. In this way, a torque is exerted in the direction of arrow D4 by the magnetic attractive force and the magnetic repulsive force generated between each magnetic pole face (illustrated by N in the figure) and pole teeth 115b and 116b, and magnet 123 moves in the direction of arrow D4. This torque in the direction of arrow D4 is exerted even by the restoring force of elastic member 180.

The reverse current that flows in coil 114b of coil portion 114 flows until the position of magnet 123 with respect to pole teeth 115b and 116b is in the state illustrated in FIG. 6B. FIG. 6B illustrates magnet 123 after the movement to arrow D4.

In FIG. 6B, as a result of rotation of magnet 123 in the reverse direction (rotation in the direction of arrow D4), each pole face in magnet 123 is about to stop at a facing position with pole teeth 115b and 116b excited by opposing magnetic poles. For example, magnetic pole face S1 is about to stop at a position completely facing pole tooth 115b-1 (S pole) and pole tooth N adjacent in the movement direction side of magnet 123. Moreover, edge SE1 of pole face S1 of magnet 123 is located at this position so as to face edge side 1152 located on the rotation direction (D4 direction) side of magnet 123 among edge sides spaced apart in the circumferential direction in pole teeth 115b. When magnet 123 is about to reach this position, a torque is also exerted on magnet 123 in the direction (direction of arrow D1) opposite to the direction of arrow D4 by repulsion to a pole tooth of the same magnetic pole close to magnet 123. Moreover, magnet 123 (movable body 120) is in a state where it is biased to the neutral position side (D1 side) by the restoring force of elastic member 180. Edge SE2 and one edge of facing pole tooth N are on the same straight line extending radially with respect to rotary shaft 24.

Subsequently, by making the forward current flow in coil portion 114, the operation illustrated in FIGS. 5 and 6A is performed again and the operation illustrated in these FIGS. 5, 6A and 6B is repeated. In this way, movable body 120 of actuator 100 performs reciprocal rotation, that is, vibrates, about rotary shaft 122 and the neutral position, and outputs the reciprocal vibration force to the outside through vibration, and arm 121.

Next, an alternating current supplied to coil 114b of immovable body 110 in each state illustrated in FIGS. 5, 6A and 6B is briefly described.

FIGS. 7A and 7B illustrate a period of the alternating current supplied from alternating current supplier 190 to coil 114b of immovable body 110 through substrate 112 in the actuator of the present embodiment.

The alternating current flowing in the coil may be a pulse wave of frequency $f_0$ as illustrated in FIG. 7A and may be a sine wave of frequency $f_0$ as illustrated in FIG. 7B.

The forward current is supplied at timing t1 illustrated in FIGS. 7A and 7B in the state of FIG. 5, the current direction is switched as illustrated in timing t2 of FIGS. 7A and 7B in the state of FIG. 6A, and the reverse current at timing t3 illustrated in FIGS. 7A and 7B is supplied when magnet 123 rotates toward the position in FIG. 6B and returns to the state of FIG. 5. Moreover, in the state of FIG. 6B, the current direction is switched as illustrated in timing t4 in FIGS. 7A and 7B, magnet 123 rotates toward the state of FIG. 6A and the forward current at timing t5 illustrated in FIGS. 7A and 7B is supplied when it returns to the state of FIG. 5. This is operation for one period, and, by repeating such operation, movable body 120 repeats the displacement operation illustrated in FIGS. 6A and 6B through the state of FIG. 5 and thereby performs reciprocal rotary vibration.

Thus, according to the present embodiment, it is possible to realize an actuator with a simple magnetic circuit configuration that can realize a high output at a low material cost and can be driven at a constant speed.

Moreover, magnet 123 is arranged annularly so as to face pole teeth 115b and 116b arranged in such a manner that polarities alternately vary on the circumferential surface of immovable body 110, it is possible to provide a drive source over the entire inner circumferential surface of magnet 123 facing pole teeth 115b and 116b, and it is possible to realize an actuator with a high conversion efficiency.

Thus, according to the present embodiment, the magnetic attractive force and the magnetic repulsive force are generated over the entire circumferential surface of magnet 123 and the largest torque can be generated.

Moreover, in actuator 100, movable body 120 performs reciprocal rotation, that is, reciprocal rotary vibration, and this reciprocal rotary vibration is output to the outside through arm 121. In a case where a toothbrush portion is coupled with arm 121, which includes in a head portion a bristle portion that is perpendicular to the axial direction of rotary shaft 122, unlike the conventional art, it is possible to make the toothbrush portion perform reciprocal rotary vibration and perform rolling polish in a simple structure. Moreover, in a case where actuator 100 is used for an electric razor, an electric shaver and an electric head hair trimming appliance or the like as an electric beauty appliance, it is possible to perform reciprocal vibration of blades by coupling the blades with arm 121.

Thus, actuator 100 satisfies Equations 2 and 3 and is driven by a resonance phenomenon using the resonance frequency given by Equation 1. In this way, in actuator 100, the power consumed in a stationary state is only for a loss due to load torque and a loss due to friction or the like, and it is possible to drive movable body 120 with low power consumption, that is, it is possible to make movable body 120 perform reciprocal rotary vibration with low power consumption. As described above, according to actuator 100 of the present embodiment, it is possible to realize reciprocal rotary motion of blades in portable electric beauty appliances such as an electric toothbrush, an electric razor, an electric shaver and an electric head hair trimming appliance, with a simple structure and low power consumption without using a drive transfer mechanism different from a drive source including actuator 100.

Moreover, since movable body 120 is supported in a movable manner by elastic member (torsion coil spring) 180, the spring lifetime becomes long, a long term drive is possible and high reliability can be ensured.

Embodiment 2

Figure 8:
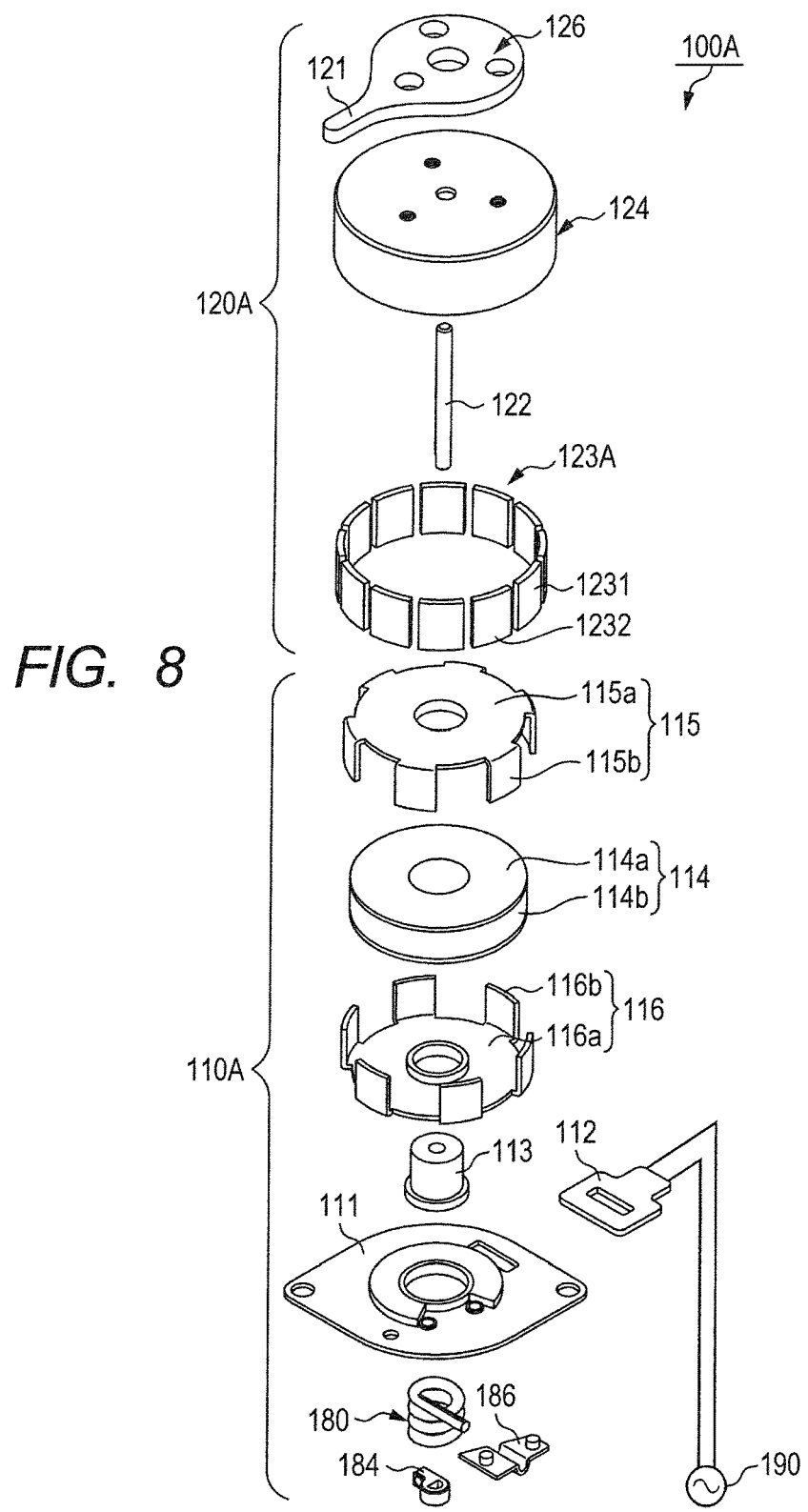
FIG. 8 is an exploded perspective view of an actuator according to Embodiment 2 of the present invention.
Figure 9:
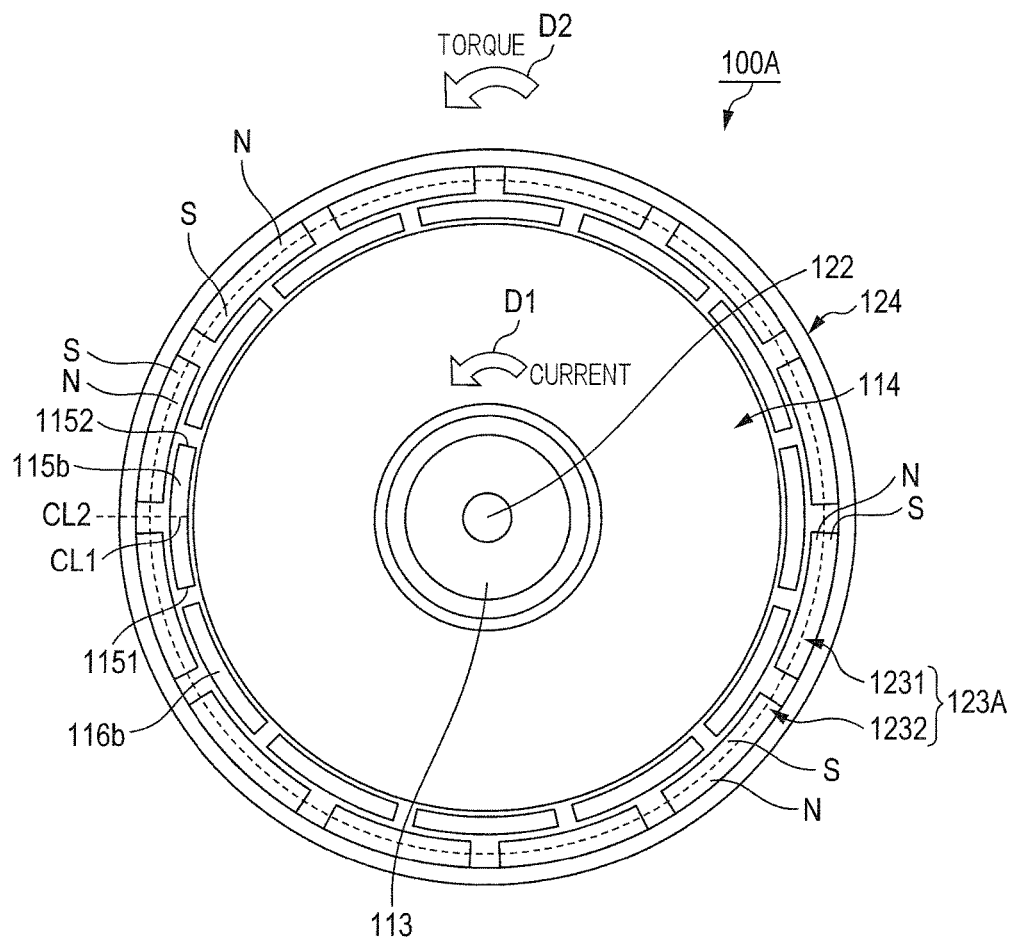
FIG. 9 is a plan cross-sectional view illustrating a magnetic circuit of the actuator.

FIG. 8 is an exploded perspective view of actuator 100A according to Embodiment 2 of the present invention and FIG. 9 is a plan cross-sectional view illustrating a magnetic circuit of this actuator 100A.

Actuator 100A according to this Embodiment 2 employs the configuration of actuator 100 based on Embodiment 1 illustrated in FIGS. 1 to 7, in which magnet 123 is replaced with magnet 123A. Therefore, actuator 100A has a basic configuration similar to actuator 100, the same reference numerals are assigned to the same components and the explanation is omitted.

Actuator 100A illustrated in FIGS. 8 and 9 includes immovable body 110A configured in the same way as immovable body 110 of actuator 100 of Embodiment 1, movable body 120A, elastic member 180 that supports movable body 120A to immovable body 110A in a movable manner and alternating current supplier 190. The appearance of this actuator 100A is similar to actuator 100.

In actuator 100A illustrated in FIGS. 8 and 9, movable body 120A moves with respect to immovable body 110A by the power supplied from alternating current supplier 190, arm 121 of movable body 120A rotates in the forward and reverse direction (see the arrow direction in FIG. 1) within a predetermined angular range and the rotation is output to the outside as a reciprocal rotary vibration.

Movable body 120A in actuator 100A adopts the configuration of movable body 120 in Embodiment 1, in which cylindrical magnet 123 is replaced with magnet 123A including multiple division segments.

That is, a movable body 120A includes rotary shaft 122, magnets 123A and magnet fixing portion 124 that fixes rotary shaft 122 and magnet 123A.

Magnet 123A is formed of a plurality (here, 12) of magnet segments 1231, 1232, . . . , which are arranged on the circumferential surface and having different polarities from adjacent segments in the circumferential direction. The magnetic pole faces of these magnet segments 1231 and 1232 are arranged so as to face pole teeth 115b and 116b of immovable body 110A. A ferrite magnet is used as magnet segments 1231 and 1232. Since the thermal characteristic of the ferrite magnet is higher than that of a neodymium bond magnet, actuator 100A using the ferrite magnet can be also used as a vehicle actuator.

Magnets 123A are fixed to magnet fixing portion 124 such that faces (magnetic pole faces) of alternately different polarities like N, S, N, S, N, . . . , face magnet segments 1231 and 1232 according to pole teeth 115b and 116b of immovable body 110A.

To be more specific, magnet segments 1231 and 1232 are attached to the inner circumferential surface of a tubular portion in cup-shaped magnet fixing portion 124 in such a manner that the magnetic properties of adjacent faces in the circumferential direction are different. The lengths of magnet segments 1231 and 1232 in the circumferential direction are longer than the lengths of pole teeth 115b and 116b in the circumferential direction.

Magnets 123A are fixed to rotary shaft 122 by magnet fixing portion 124 in the same way as magnet 123 of Embodiment 1.

In the magnetic faces of magnet segments 1231 and 1232 of magnets 123A, pole teeth 115b and 116b are located at positions at which center positions CL1 in the circumferential direction coincide positions CL2 partitioning magnet segments 1231 and 1232 in the radial direction with respect to the rotational center. Partition positions CL2 are positions at which the polarities (magnetic pole faces) of magnet segments 1231 and 1232 are reversed in magnets 123A.

Positions CL2 are the intermediate positions between magnet segments 1231 and 1232. The positions at which center positions CL1 and positions CL2 coincide on the same straight line in the radial direction with respect to rotary shaft 122 (that is, in a radial fashion) is a rotation neutral position of movable body 120A.

Thus, actuator 100A differs from actuator 100 only in that the magnetized faces (magnetic pole faces) of magnet 123 configured as a single piece previously is formed of separate magnet segments. Therefore, operation similar to actuator 100 is performed by supplying an alternating current to coil 114b, and it is possible to provide the same effect as actuator 100.

Moreover, it is possible to easily manufacture actuator 100A as compared with a case where magnets provided in movable body 120 are magnetized to have alternately different magnetic properties over the cylindrical inner circumferential surface, corresponding to the pole teeth of immovable body 110. That is, in a case where the magnets arranged with alternately different magnetic pole faces in the circumferential direction are manufactured, it only has to attach magnet segments 1231 and 1232 to the inner circumferential surface of the tubular portion of magnet fixing portion 124 such that magnetic pole faces change alternately. In this way, it is possible to easily manufacture actuator 100A without a magnetization step.

Embodiment 3

Figure 10:
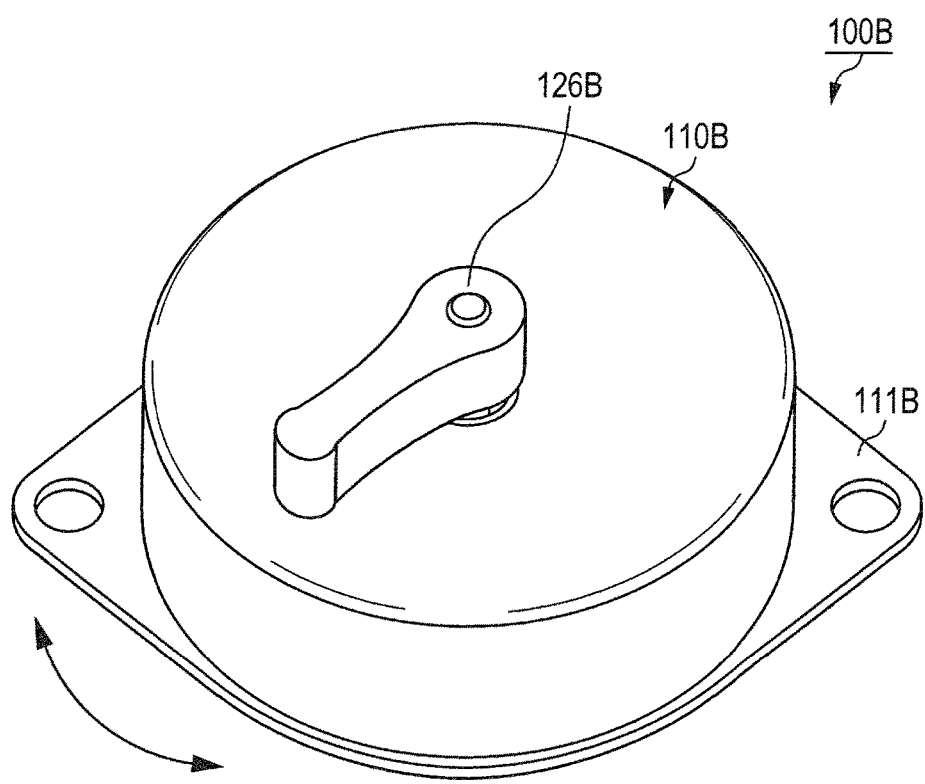
FIG. 10 is a perspective view illustrating an actuator according to Embodiment 3 of the present invention.
Figure 11:
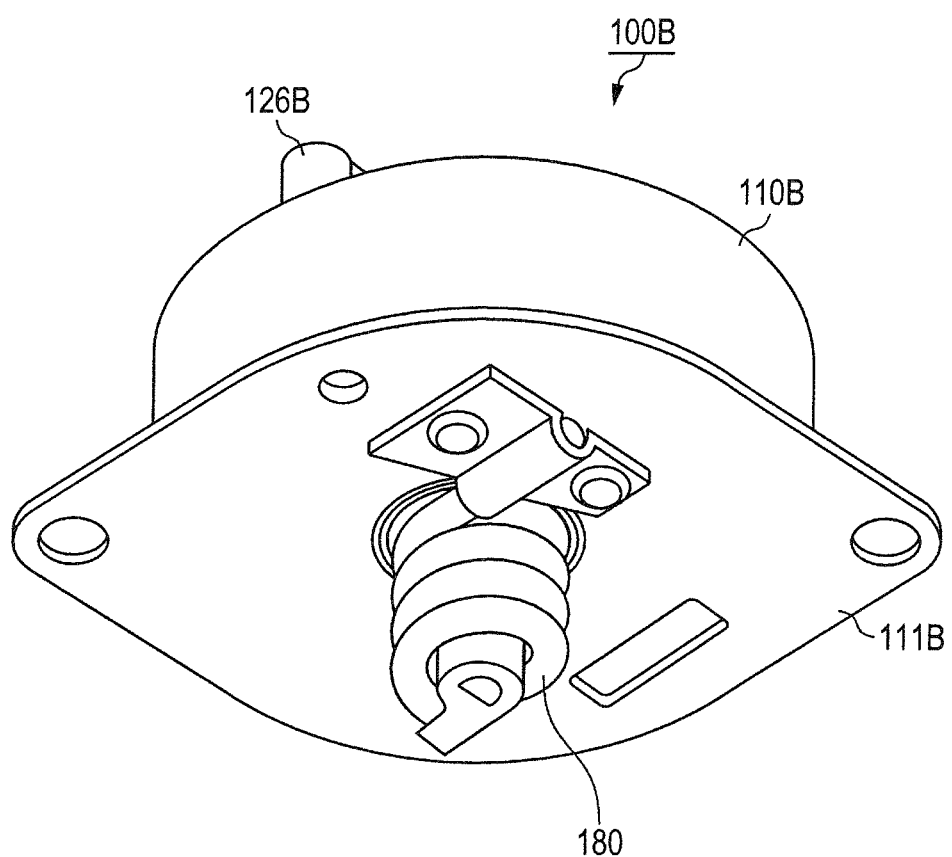
FIG. 11 is a perspective view illustrating a lower surface of the actuator.
Figure 13:
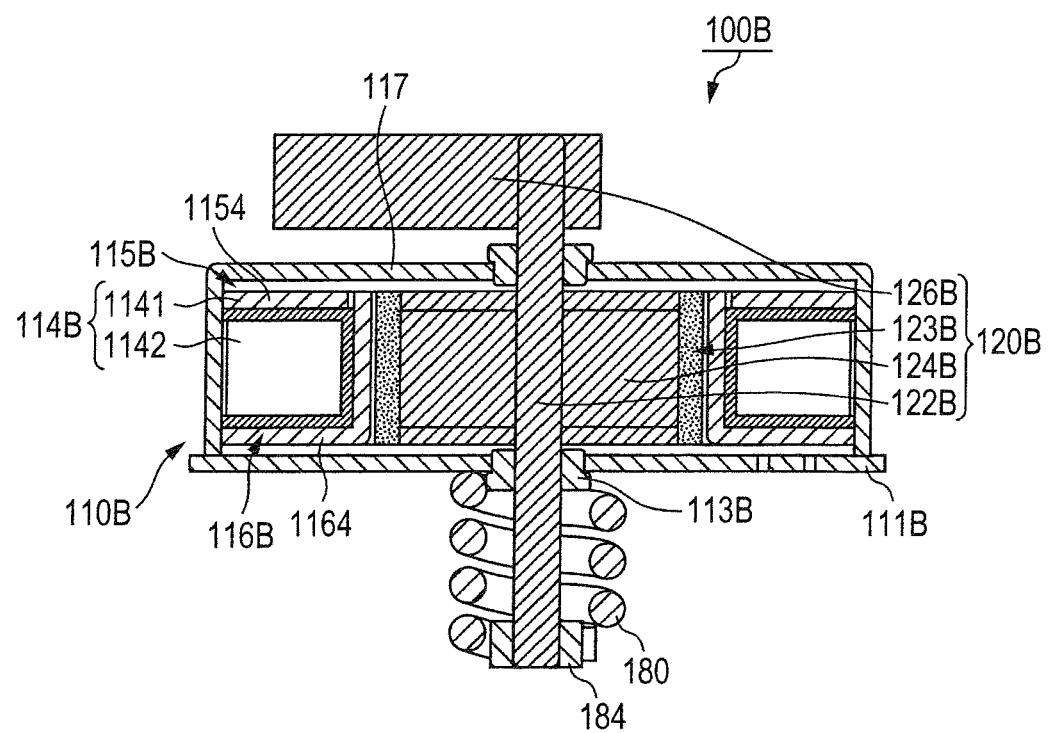
FIG. 13 is a schematic cross-sectional view illustrating a main part configuration in the actuator.
Figure 14:
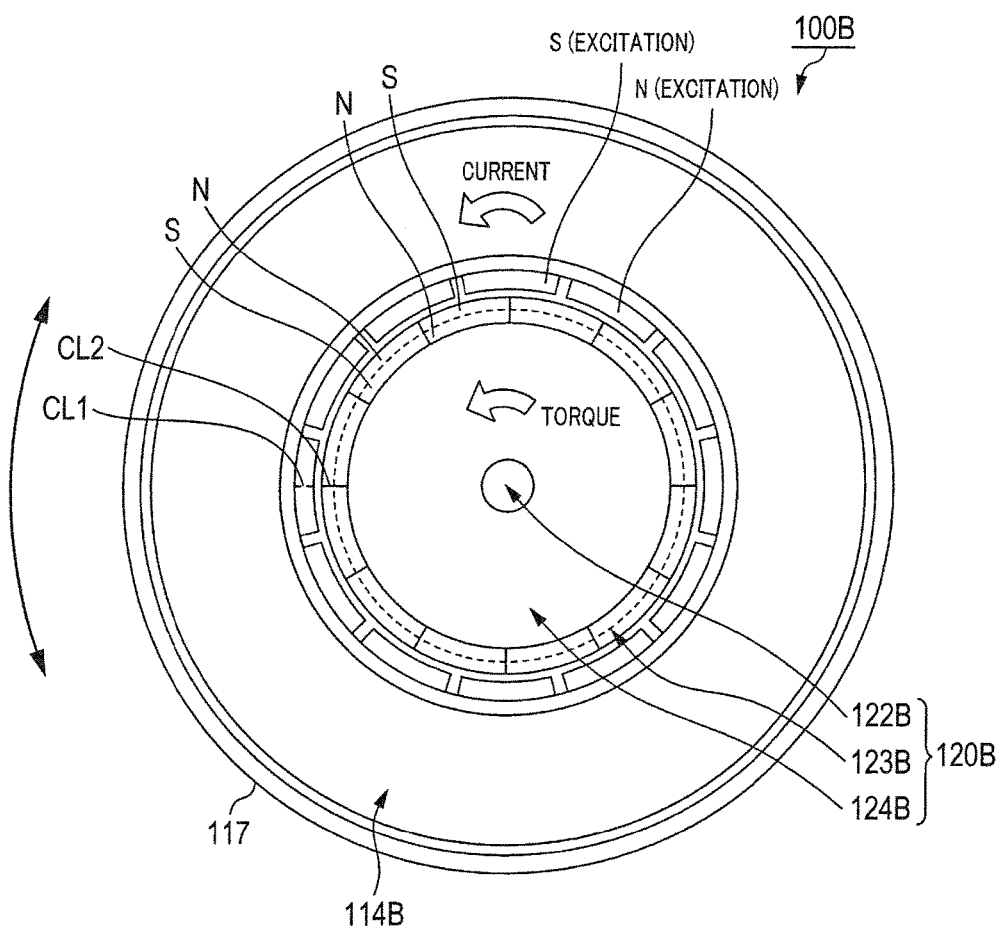
FIG. 14 is a plan cross-sectional view illustrating a magnetic circuit of the actuator.

FIG. 10 is a perspective view illustrating actuator 100B according to Embodiment 3 of the present invention and FIG. 11 is a perspective view illustrating the lower surface of this actuator 100B. Moreover, FIG. 12 is an exploded perspective view of main part of this actuator 100B, FIG. 13 is a schematic cross-sectional view illustrating a main part configuration in this actuator 100B and FIG. 14 is a plan cross-sectional view illustrating a magnetic circuit of this actuator 100B.

Here, actuator 100B according to this Embodiment 3 has a basic configuration similar to actuator 100 according to Embodiment 1 illustrated in FIGS. 1 to 7, only except for that the positional relationship between the immovable body and the movable body is different. To be more specific, while actuator 100 of Embodiment 1 and actuator 100A of Embodiment 2 are an outer rotor type, actuator 100B is an actuator of an inner rotor type. Therefore, the same reference numerals are assigned to components having the same function and the explanation is omitted.

Figure 12:
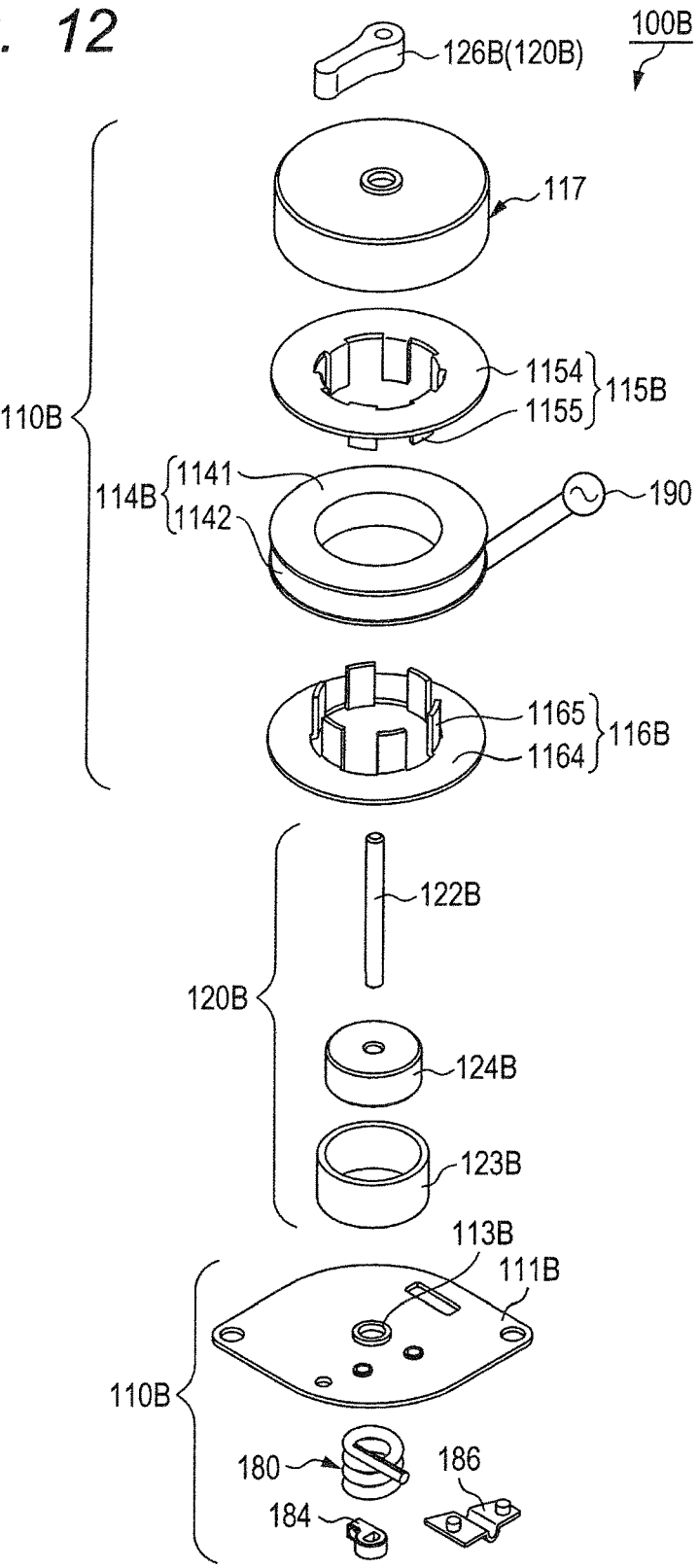
FIG. 12 is an exploded perspective view of main part of the actuator.

Actuator 100B illustrated in FIGS. 10 and 11 has immovable body 110B, movable body 120B (see FIG. 12), elastic member (elastic support) 180 (see FIG. 11) that supports movable body 120B to immovable body 110B in a movable manner, and alternating current supplier 190 (see FIG. 12).

In actuator 100B illustrated in FIG. 10, output arm 126B of movable body 120B rotates in the forward and reverse direction (the arrow direction of in FIG. 10) within a predetermined angular range by an alternating current wave supplied from alternating current supplier 190 (see FIG. 12) and the rotation is output to the outside as a reciprocal rotary vibration.

Immovable body 110B illustrated in FIGS. 11 to 13 has base plate 111B, annular coil portion 114B, comb-toothed upper and lower yokes 115B and 116B having pole teeth 1155 and 1165 arranged along the inner circumferential surface of coil portion 114B, and case 117.

In immovable body 110B as illustrated in FIGS. 11 to 13, bearing 113B is attached in communication with the opening provided in the center of base plate 111B. Rotary shaft 122B of movable body 120B is inserted in the opening of base plates 111B and bearing 113B. Bearing 113B supports rotary shaft 122B of movable body 120B in a rotatable manner.

Coil portion 114B sandwiched in the axial direction of rotary shaft 122 by upper and lower yokes 115B and 116B is arranged on this bearing 113B so as to enclose movable body 120B.

Coil portion 114B is configured by winding coil 1142 to bobbin 1141. Bobbin 1141 and coil 1142 are used together to create a drive source of actuator 100B. Bobbin 1141 is coaxial with rotary shaft 122B and an axis of coil 1142.

The winding wire of coil 1142 is connected to a substrate (not illustrated) and connected to an external terminal through the substrate. The alternating current (alternating-current voltage) is supplied from alternating current supplier 190 to coil 1142 through the external terminal.

Upper and lower yokes 115B and 116B are made of a magnetic material and respectively have comb-toothed pole teeth 1155 and 1165 which extend vertically from the inner edge of body plate portions 1154 and 1164 each having a shape of an annular and flat plate. Upper and lower yokes 115B and 116B are arranged in a mutually non-contact manner so as to sandwich coil portion 114B in the axial direction of rotary shaft 122. Respective body plate portions 1154 and 1164 of upper and lower yokes 115B and 116B are arranged facing upper and lower surfaces of coil 114B which are spaced apart in the axial direction of rotary shaft 122, and respective pole teeth 1155 and 1165 of upper and lower yokes 115B and 116B are alternately located so as to enclose the inner circumferential surface of coil portion 114B.

To be more specific, upper yoke 115B is fitted from the upper side of coil portion 114B, its body plate portion 1154 faces the upper surface of coil portion 114B and pole teeth 1155 are located in a comb tooth manner (spaced at a predetermined interval) along the inner circumferential surface of coil portion 114B. Lower yoke 116B is fitted from the lower side of coil portion 114B, its body plate portion 1164 faces the lower surface of coil portion 114B and pole teeth 1165 are uniformly arranged between pole teeth 1155 located along the inner circumferential surface of coil portion 114B.

The number of poles of pole teeth 1155 and 1165 of upper and lower yokes 115B and 116B are equal to the number of magnetic poles of magnets 123B (described later) of movable body 120B.

With this configuration, when an alternating current is supplied to coil 1142, upper yoke 115B and lower yoke 116B are excited respectively to have mutually different polarities, and pole teeth 1155 and 1165 of upper and lower yokes 115B and 116B are also excited by different polarities. That is, in the inner circumferential surface of coil portion 114B, different magnetic pole faces are alternately arranged along the inner circumferential surface.

The polarities of these pole teeth 1155 and 1165 alternately change by the forward-direction current and the reverse-direction current supplied to coil portion 114B.

These coil portions 114B are attached to base plate 111B so as to be covered with cup-shaped case 117 from the upper side.

Magnet 123B of movable body 120B is arranged at a predetermined interval so as to face pole teeth 1155 and 1165 arranged along the inner circumferential surface of coil portion 114B.

Here, although pole teeth 1155 and 1165 are configured to have 12 poles, which are the same as a corresponding magnet (described later), the number of poles is not limited to this and may be two or more in a variation of the present invention.

Movable body 120 has rotary shaft 122B, magnet 123B and rotor 124B that fixes magnet 123B to rotary shaft 122B.

As illustrated in FIG. 14, magnet 123B is cylindrical and magnetized with multiple (12, in this case) poles, and, for example, a neodymium bond magnet is employed.

To be more specific, magnet 123B is magnetized so as to have magnetic pole faces of alternately-different polarities in the outer circumferential surface facing pole teeth 1155 and 1165. The length of each of the magnetized faces of N pole, S pole, . . . , in the circumferential direction (here, the direction perpendicular to the rotary shaft in the circumferential direction) substantially the same as the length of pole teeth 1155 and 1165 in the circumferential direction. Here, although magnet 123B is configured as a single piece in a cylindrical shape, positions between adjacent magnetized faces at which the polarity is reversed are expediently illustrated by partition lines in FIG. 14.

Rotary shaft 122B is press-fixed into the center of magnet 123B and magnet 123B is externally fitted to the outer circumferential surface of rotor 124B having a predetermined radius. Magnet 123B, rotary shaft 122B, rotor 124B and output arm 126B form movable body 120B.

In the magnetized faces (N pole faces and S pole faces) of magnet 123B, pole teeth 1155 and 1165 are located at positions at which center positions CL1 in the circumferential direction coincide positions CL2 (positions at which the magnetized faces S and N are partitioned) between the N magnetized face and the S magnetized face in a radial direction with respect to the a rotational center. Also, a position at which center position CL1 and position CL2 overlap on the same straight line in the radial direction with respect to rotary shaft 122B (that is, in a radial fashion) is an operation neutral position of movable body 120B.

Output arm 126B that extends perpendicularly to rotary shaft 122B above case 117 is fixed to one end of rotary shaft 122B which is passed through the top plate part of case 117. Actuator 100B transmits a drive force to the outside through this output arm 126B.

The other end of this rotary shaft 122B is passed through base plate 111B. This other end is fixed to base plate 111B by elastic member 180 on the back side of base plate 111B.

Elastic member 180 elastically supports movable body 120B with respect to immovable body 110B. Here, a torsion coil spring is employed as elastic member 180.

One end of the torsion coil spring that is elastic member 180 is fixed to rotary shaft 122B by shaft fixing part 184 and the other end is fixed to base plate 111B by base fixing part 186.

Elastic member (torsion coil spring) 180 is positioned in such a manner that on the outer circumferential surface of magnet 123B of movable body 120B the partition positions between adjacent magnetized faces N and S of different magnetic properties are located at the center in the circumferential direction of respective pole teeth 115S and 116S of immovable body 110B.

Moreover, elastic member (torsion coil spring) 180 can acquire a given spring constant with respect to the rotation direction of magnet 123B and movable body 120B is movable in the circumferential direction.

In actuator 100B of the above configuration, upper and lower yokes 115B and 116B, i.e. pole teeth 115S and 116S, are magnetized by the alternating current wave input to coil 1142, and the magnetic attractive force and the magnetic repulsive force are efficiently generated for magnet 123B of movable body 120B. In this way, magnet 123B of movable body 120B moves back and forth in the circumferential direction with the center of pole teeth 115S and 116S being the neutral position, and, as a result of this, magnet 123B itself performs reciprocal rotation about rotary shaft 122B.

This actuator 100B satisfies Equations 2 and 3 and is driven by a resonance phenomenon using the resonance frequency given by Equation 1. This drive is the same as actuator 100 and therefore the explanation is omitted. The power consumed in a stationary state is only for a loss due to load torque and a loss due to friction or the like, and it is possible to drive movable body 120B with low power consumption, that is, it is possible to make movable body 120B perform reciprocal rotary vibration with low power consumption.

Similar to actuator 100, actuator 100B is applicable to electric beauty appliances such as an electric toothbrush, an electric razor, an electric shaver and an electric clipper. In this way, it is possible to realize reciprocal rotary motion of blades in these electric beauty appliances, with low power consumption without using a drive transfer mechanism different from a drive source.

Here, in each embodiment, the operation angle that is the reciprocal rotation range, that is, the operation angle that is the oscillation range can be enlarged by widening the magnetic pole faces of pole teeth facing the magnetic pole faces of magnets 123, 123A and 123B as much as possible.

Various modifications may be made to the above-mentioned present invention without departing from the spirit of the present invention, and it is natural that the present invention covers such modifications.

INDUSTRIAL APPLICABILITY

An actuator and an electric beauty appliance according to the present invention provide an effect of realizing high output with high energy conversion efficiency in a simple configuration, and are useful to be applied to an electric razor an electric toothbrush, and so on.

What is claimed is:

1. An actuator comprising:
   a movable body including a cylindrical magnet portion having on an inner circumferential surface thereof alternating N pole faces and S pole faces along a circumferential direction thereof;
   an immovable body including an outer circumferential surface facing the inner circumferential surface of the magnet portion, pole tooth faces arranged in the outer circumferential surface along the circumferential direction, and a coil configured to excite the pole tooth faces; and
   a torsion coil spring that supports the movable body to the immovable body in a reciprocally rotatable manner about a rotary shaft which is a part of the movable body and biases the movable body to a rotation neutral position,
   wherein the coil receives an alternating current of a frequency substantially equal to a resonance frequency of the movable body that is determined by an inertia of the movable body and the spring constant in a torsion direction of the torsion coil spring to excite the pole tooth faces to have alternately different polarities in the circumferential direction,
   wherein one end of the torsion coil spring is fixed to one end of the rotary shaft of the movable body, the other end is fixed to the immovable body, the torsion direction of the torsion coil spring is arranged to be coaxial with the rotary shaft, and the torsion coil spring supports the movable body to enable the movable body to vibrate at the resonance frequency of the movable body.

2. The actuator according to claim 1, wherein the rotation neutral position is a position at which center positions of the pole tooth faces in the circumferential direction and boundary positions between the pole faces of the magnet portion face each other.

3. The actuator according to claim 1, wherein the magnet portion includes a plurality of separate segments each having one of the N pole face or the S pole face.

4. An electric beauty appliance comprising the actuator according to claim 1.

* * * * *